(12) United States Patent
Francis et al.

(10) Patent No.: US 12,262,915 B2
(45) Date of Patent: *Apr. 1, 2025

(54) TRACTION APPLYING DEVICES FOR LEAD REMOVAL SYSTEMS

(71) Applicant: KONINKLIJKE PHILIPS N.V., Eindhoven (NL)

(72) Inventors: Nathan C. Francis, Colorado Springs, CO (US); Matthew Magee, Colorado Springs, CO (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/211,771

(22) Filed: Jun. 20, 2023

(65) Prior Publication Data

US 2023/0346427 A1 Nov. 2, 2023

Related U.S. Application Data

(63) Continuation of application No. 16/997,558, filed on Aug. 19, 2020, now Pat. No. 11,678,908.

(60) Provisional application No. 62/896,887, filed on Sep. 6, 2019.

(51) Int. Cl.
*A61B 17/34* (2006.01)
*A61B 17/3205* (2006.01)
*A61N 1/05* (2006.01)
*A61B 90/00* (2016.01)

(52) U.S. Cl.
CPC ...... *A61B 17/3468* (2013.01); *A61B 17/3205* (2013.01); *A61N 1/056* (2013.01); *A61B 2090/066* (2016.02); *A61N 2001/0578* (2013.01)

(58) Field of Classification Search
CPC .......... A61B 17/3468; A61B 17/32053; A61B 2017/22075; A61B 2017/00398; A61B 2090/064; A61N 2001/0578
See application file for complete search history.

(56) References Cited

U.S. PATENT DOCUMENTS

| | | | |
|---|---|---|---|
| 5,810,717 | A | 9/1998 | Maeda |
| 6,167,315 | A | 12/2000 | Coe |
| 6,324,434 | B2 | 11/2001 | Coe |
| 6,772,014 | B2 | 8/2004 | Coe |
| 7,499,756 | B2 | 3/2009 | Bowe |
| 9,032,806 | B2 | 5/2015 | Verma |
| 9,413,896 | B2 | 8/2016 | Bowe |
| 9,603,618 | B2 | 3/2017 | Carver |
| 9,801,650 | B2 | 10/2017 | Taylor |

(Continued)

FOREIGN PATENT DOCUMENTS

EP   3369403 A1 * 9/2018 ......... A61B 17/3468

*Primary Examiner* — Sarah W Aleman

(57) ABSTRACT

A lead removal system includes a lead removal device comprising a sheath. The sheath includes a distal separating member configured to separate an implanted lead from adjacent tissue. The sheath also includes a sheath lumen configured to receive a lead engagement device and the implanted lead. A traction applying device is coupled to the lead removal device. The traction applying device is configured to be secured to the lead engagement device and apply traction to the lead engagement device and the implanted lead as the distal separating member of the sheath separates the implanted lead from adjacent tissue.

12 Claims, 6 Drawing Sheets

(56) References Cited

U.S. PATENT DOCUMENTS

| | | |
|---|---|---|
| 9,889,294 B2 | 2/2018 | Kalmann |
| 9,918,737 B2 | 3/2018 | Carver |
| 9,980,743 B2 | 5/2018 | Grace |
| 10,136,913 B2 | 11/2018 | Carver |
| 2013/0116704 A1 | 5/2013 | Geistert |
| 2013/0231678 A1 | 9/2013 | Wenderow |
| 2015/0231313 A1* | 8/2015 | O'Keefe ............... A61M 25/00 604/266 |
| 2015/0367123 A1 | 12/2015 | Kalmann |
| 2016/0345898 A1 | 12/2016 | Verma |
| 2017/0172622 A1 | 6/2017 | Grace |
| 2017/0216574 A1 | 8/2017 | Booker |
| 2017/0303930 A1* | 10/2017 | Haller .............. A61B 17/12013 |
| 2018/0221055 A1 | 8/2018 | Grace |
| 2019/0216521 A1 | 7/2019 | Chhatrala |
| 2020/0352552 A1 | 11/2020 | Rousso |

\* cited by examiner

TRACTION APPLYING DEVICES FOR LEAD REMOVAL SYSTEMS

CROSS-REFERENCE TO RELATED APPLICATION

This application is a continuation of U.S. patent application Ser. No. 16/997,558, filed Aug. 19, 2020, now U.S. Pat. No. 11,678,908, which claims the benefit of U.S. Provisional Patent Application No. 62/896,887, filed Sep. 6, 2019, each of which is hereby incorporated by reference herein.

FIELD OF THE DISCLOSURE

The devices described herein generally relate to systems for removing implanted leads, such as cardiac implantable electronic device ("CIED") leads, from subjects' bodies, and more specifically relate to devices for applying traction to implanted leads during removal procedures.

BACKGROUND

Various medical procedures attach wire-like devices to internal portions of a subject's body, such as an electrical lead for a cardiac implantable electronic device ("CIED"). CIED leads are electrically conductive wires which run to an electrode that is attached to an inner wall of a subject's heart. CIED leads are usually implanted with the intention that they will remain in the subject for several years. However, CIED leads sometimes need to be removed for a variety of reasons including infection, malfunction, venous occlusion, advisory, etc.

Various systems have been provided to remove CIED leads from subjects' bodies. Some lead removal systems also facilitate separating CIED leads from any fibrous tissue that has grown over the lead. For example, some systems include an elongated lead engagement device that is inserted in a hollow space running down the center of the CIED lead (a "lumen"). An example of an elongated lead engagement device is Lead Locking Device (LLD) manufactured by the Spectranetics Corporation, which is part of Koninklijke Philips N. V. During use of the elongated lead engagement device, a physician grasps and applies tension to the lead engagement device. The elongated lead engagement device, in turn, applies tension or "traction" to the CIED lead, while the physician advances a lead removal device over the CIED lead and the lead engagement device. The distal end of the lead removal device includes a means for dilating and or cutting tissue surrounding the CIED lead. So, as the lead removal device advances over the lead engagement device and the CIED lead, the lead engagement device separates the CIED lead from any fibrous tissue that has grown over the lead.

These lead removal systems and associated methods have some potential drawbacks. For example, the amount of traction applied to CIED leads by an individual physician or different physicians between separate lead extraction procedures may vary. It has been asserted that some adverse events (that is, injuries to the subject) may result from the lack of consistent traction applied by the lead engagement device to the CIED lead. Also, the example lead-extraction procedure described above typically requires use of three hands. That is, the lead-extraction procedure generally includes at least two healthcare professionals (for example, two surgeons, or one surgeon and one clinician, nurse, fellow, or the like) handling the medical devices that are inserted in the patient; the first healthcare professional uses one hand to advance the lead removal device in the subject's vasculature and the other hand to guide the lead removal device at the insertion site on the subject. The second healthcare professional handles the lead engagement device and applies traction thereto while the first healthcare professional advances and guides the lead removal device. Alternatively, the healthcare professionals may use a different combination of three hands to perform the above actions. In any case, as one can envision, two healthcare professionals performing the lead extraction procedure could be considered cumbersome.

Accordingly, it is desirable to provide improved lead removal systems and associated methods.

SUMMARY

The present disclosure presents a lead removal system for removing an implanted lead. The implanted lead has a lead lumen for receiving and coupling to a lead engagement device. The lead removal system includes a lead removal device comprising a sheath. The sheath includes a distal separating member configured to separate the implanted lead from adjacent tissue. The sheath also includes a sheath lumen configured to receive the lead engagement device and the implanted lead. A traction applying device is coupled to the lead removal device. The traction applying device is configured to be secured to the lead engagement device and apply traction to the lead engagement device and the implanted lead as the distal separating member of the sheath separates the implanted lead from adjacent tissue.

The lead removal system according to the previous paragraph, wherein the lead removal device further comprises a handle coupled to the sheath and the traction applying device.

The lead removal system according to any of the previous paragraphs, further comprising a user input coupled to the handle, the user input being actuatable to cause the traction applying device to apply traction to the lead engagement device and the implanted lead.

The lead removal system according to any of the previous paragraphs, wherein the user input is actuatable to cause the distal separating member to separate the implanted lead from adjacent tissue.

The lead removal system according to any of the previous paragraphs, further comprising a controller operatively coupled to the user input and the traction applying device.

The lead removal system according to any of the previous paragraphs, further comprising a first user input being actuatable to cause the distal separating member to separate the implanted lead from adjacent tissue; and a second user input being actuatable to cause the traction applying device to apply traction to the lead engagement device and the implanted lead.

The lead removal system according to any of the previous paragraphs, wherein the lead removal device further comprises a handle coupled to the sheath, the traction applying device, the first user input, and the second user input.

The lead removal system according to any of the previous paragraphs, wherein the traction applying device comprises a traction drive, the traction drive being configured to rotate to apply traction to the lead engagement device and the implanted lead.

The lead removal system according to any of the previous paragraphs, wherein the traction applying device comprises a mandrel, the mandrel being configured to rotate to wind the lead engagement device therearound and thereby apply traction to the lead engagement device and the implanted lead.

The lead removal system according to any of the previous paragraphs, wherein the traction applying device is configured to pull the lead engagement device proximally through the lead removal device.

The lead removal system according to any of the previous paragraphs, further comprising the lead engagement device configured to be disposed in the sheath lumen, and the lead engagement device being configured to be inserted in the lead lumen and secure to the lead.

The present disclosure also presents a lead removal system for removing an implanted lead. The implanted lead has a lead lumen. The lead removal system includes a lead removal device comprising a sheath. The sheath comprises a distal separating member configured to separate the implanted lead from adjacent tissue and a sheath lumen configured to receive the implanted lead. A traction applying device is configured to be secured to the lead engagement device and apply traction to the lead engagement device and the implanted lead as the distal separating member of the sheath separates the implanted lead from adjacent tissue. The traction applying device includes a traction drive system, and the traction drive system includes a torque sensor, a motor, and a controller. The controller comprises non-transient computer readable medium having instructions to monitor, via the torque sensor, an amount of torque applied by the motor and adjust the amount of torque applied by the motor (or the amount of current applied to the motor) to be at a predetermined value or a predetermined range.

The lead removal system according to the previous paragraph, wherein the lead removal device further comprises a handle coupled to the sheath and the traction applying device.

The lead removal system according to any of the previous paragraphs, further comprising a user input coupled to the handle, the user input being actuatable to cause the traction applying device to apply traction to the lead engagement device and the implanted lead.

The lead removal system according to any of the previous paragraphs, wherein the user input is actuatable to cause the distal separating member to separate the implanted lead from adjacent tissue.

The lead removal system according to any of the previous paragraphs, wherein the controller is operatively coupled to the user input and the traction applying device.

The lead removal system according to any of the previous paragraphs, further comprising a first user input and a second user input, whereupon actuation of the first user input, the controller activates the tissue separating device; and whereupon actuation of the second user input, the controller activates the motor.

The lead removal system according to any of the previous paragraphs, wherein the traction applying device comprises a mandrel, the mandrel being configured to rotate to wind the lead engagement device therearound.

The lead removal system according to any of the previous paragraphs, wherein the traction applying device is configured to pull the lead engagement device proximally through the lead removal device.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (for example, $X_1$ and $X_2$) as well as a combination of elements selected from two or more classes (for example, $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
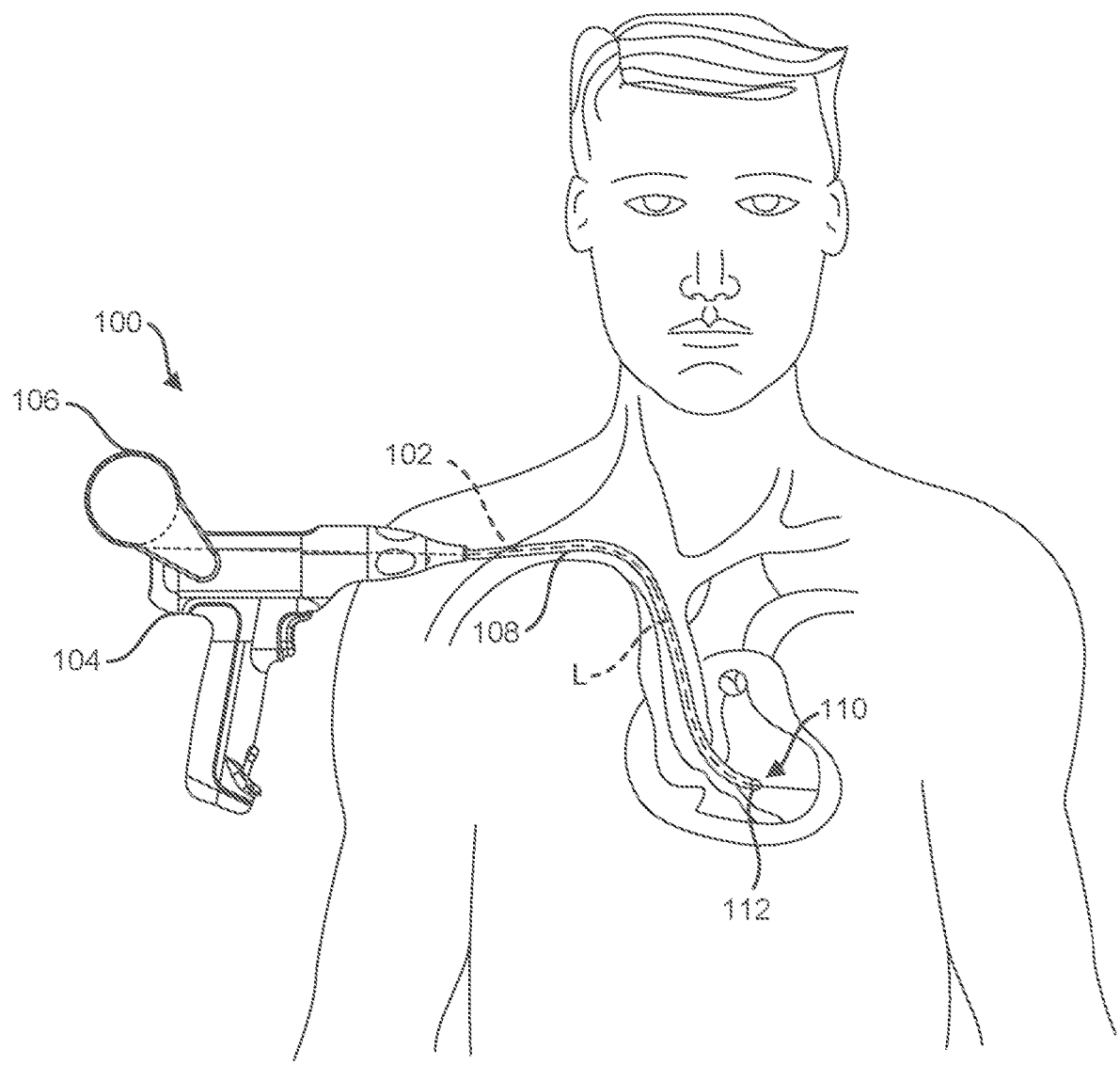
FIG. 1 illustrates a subject having a CIED lead implanted in the venous system and an embodiment of a lead removal system according to the present disclosure inserted into the venous system.

The present disclosure relates to systems for removing implanted leads, such as cardiac implantable electronic device ("CIED") leads, from subjects' bodies. FIG. 1 illustrates an exemplary embodiment of a lead removal system 100 according to the present disclosure removing an implanted lead L running along the right innominate vein past the superior vena cava ("SVC") and connected into, or about, the right ventricle of the heart. Although the system 100 is shown entering the right innominate vein, it may also enter the left innominate vein and extend through the SVC to the right ventricle of the heart. The lead removal system 100 generally includes a lead engagement device 102, a lead removal device 104, and a traction applying device 106.

The lead engagement device 102 is an elongated and flexible device that is configured to extend through the lead removal device 104 and be partially inserted in the vasculature of a subject. The lead engagement device 102 is also configured to be inserted in a lumen of the lead L (not shown) and be secured to the intermediate or distal portion of the lead L.

The lead removal device 104 includes a sheath 108 that is inserted into the vasculature of the subject. The sheath 108 includes a lumen 110 that receives the lead engagement device 102 and the lead L. The sheath 108 also includes a distal separating member 112 for cutting, dilating, or otherwise separating the lead L from adjacent tissue.

The traction applying device 106 is configured to couple to a proximal portion of the lead engagement device 102 external to the subject. The traction applying device 106 applies traction to the lead engagement device 102 and the lead L as the distal separating member 112 of the sheath 108 separates the implanted lead L from adjacent tissue. As a result, a second healthcare professional does not need to apply traction to the lead engagement device 102 and the lead L by hand during the lead extraction procedure, and the lead removal system 100 may, therefore, advantageously be used by a single healthcare professional during such procedure. Furthermore, and in contrast to applying traction by hand, the amount of traction applied to the lead engagement device 102 and the lead L will be consistent and not vary based on the healthcare professional handling the lead engagement device 102.

Figure 2:
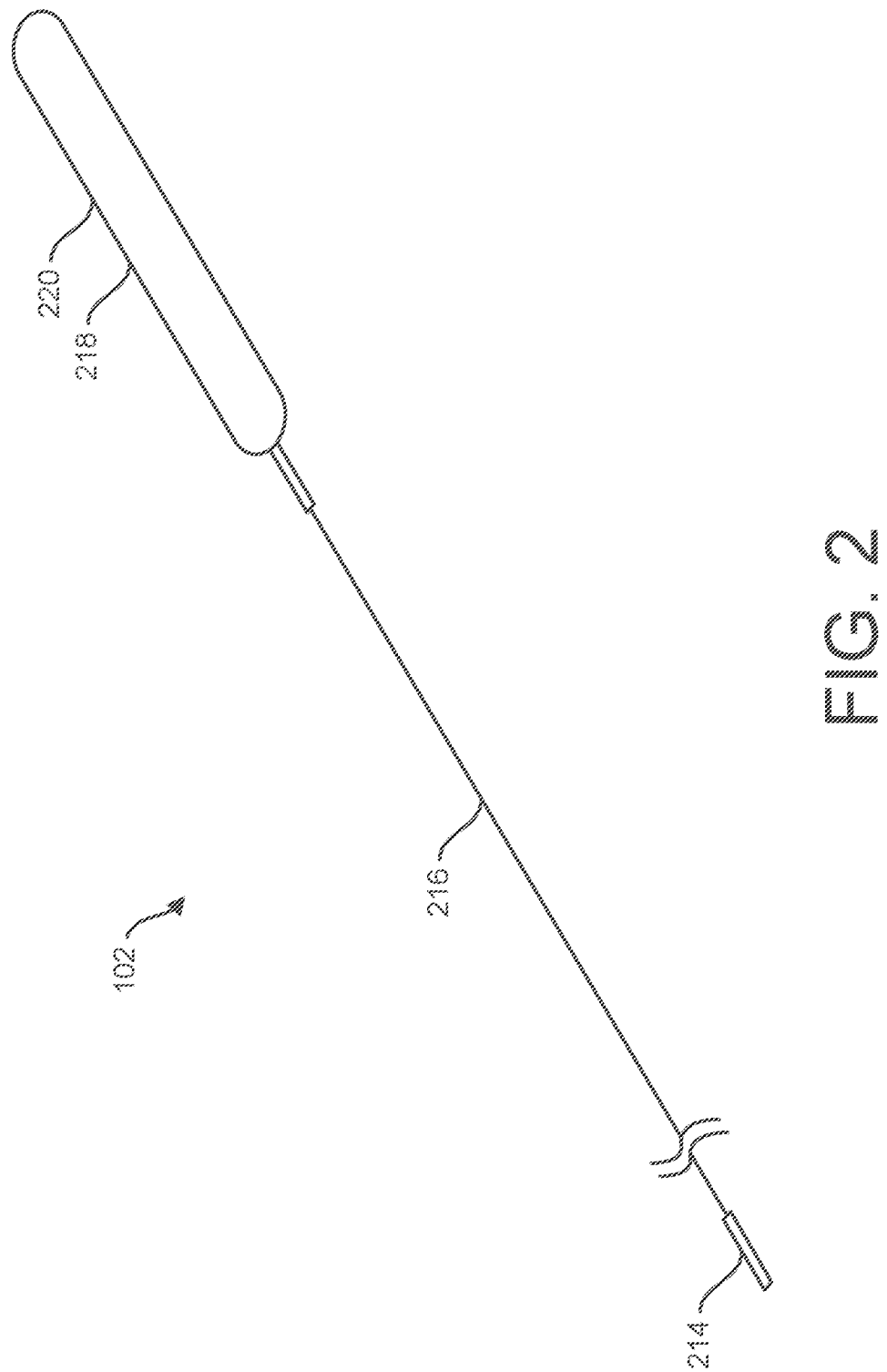
FIG. 2 illustrates a perspective view of a lead engagement device of the lead removal system of FIG. 1.

Referring now to FIG. 2 and as generally described above, lead engagement device 102 is an elongated and flexible device that is configured to be partially inserted in the vasculature of a subject and in the lumen of the lead to secure to the lead. The lead engagement device 102 includes a distal securing portion 214 that is configured to be inserted in the lumen of the lead. The distal securing portion 214 is operable to secure the lead engagement device 102 to the lead. For example, the distal securing portion 214 may be one or more expandable wires that secure the lead engagement device 102 to the lead. The distal securing portion 214 couples to an intermediate portion 216, and the intermediate portion 216 couples to a proximal coupling portion 218 opposite the distal securing portion 214. The proximal coupling portion 218 includes a coupling feature 220 for receiving traction forces. For example, the coupling feature 220 may be a loop as illustrated. Alternatively, the coupling feature 220 may take other forms, such as a handle (not shown) or an anchor (not shown). The above features of the lead engagement device 102, and the lead engagement device 102 more generally, may be similar to or the same as those described in U.S. Pat. Nos. 6,167,315; 6,324,434; 6,772,014; or 7,499,756, the disclosures of which are hereby incorporated by reference in their entireties. Also, as mentioned above, an example of a lead engagement device may include a Lead Locking Device (LLD) manufactured by the Spectranetics Corporation, which is part of Koninklijke Philips N.V.

Figure 3:
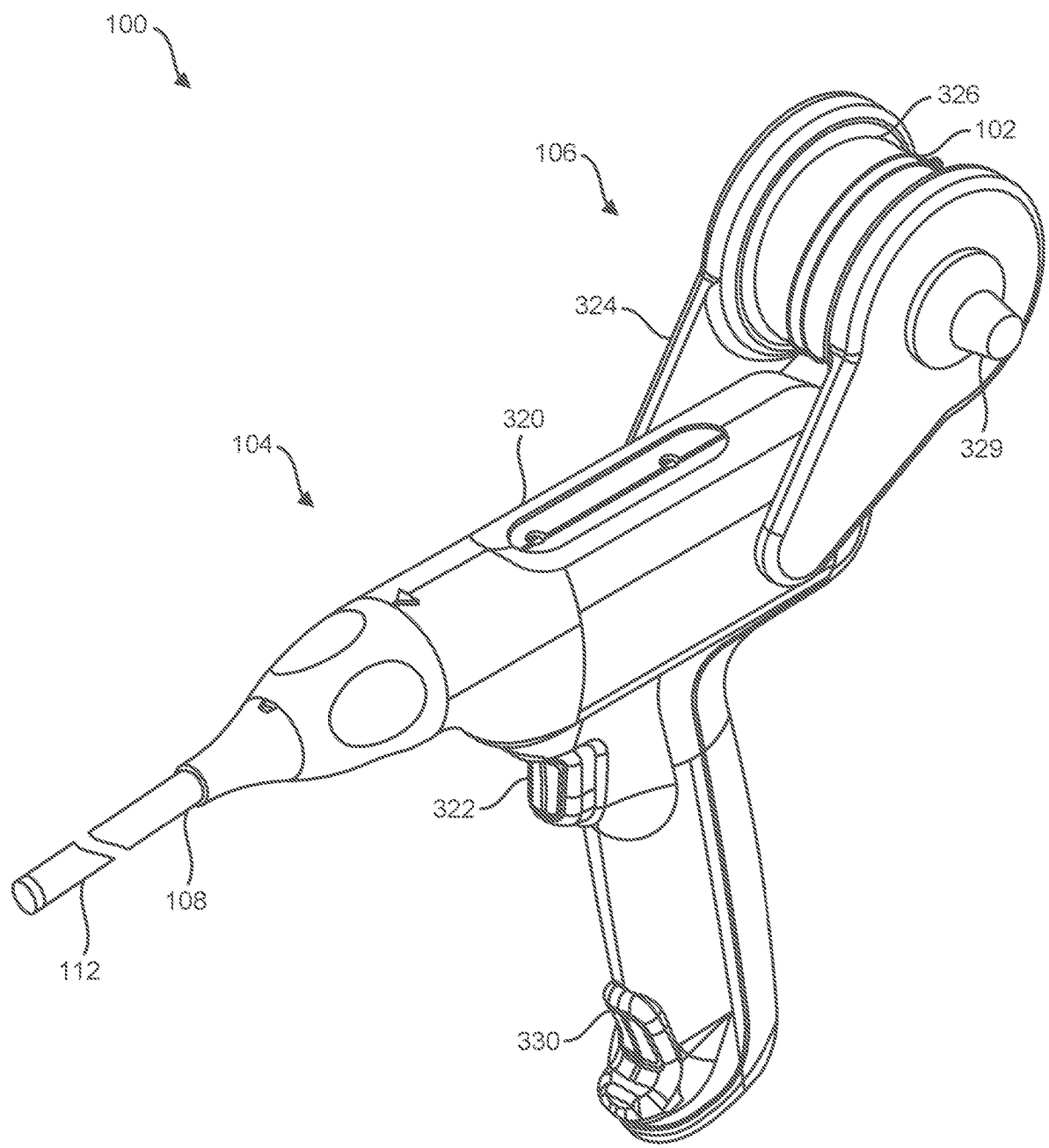
FIG. 3 illustrates a perspective view of a lead removal device and a traction applying device of the lead removal system of FIG. 1.
Figure 4:
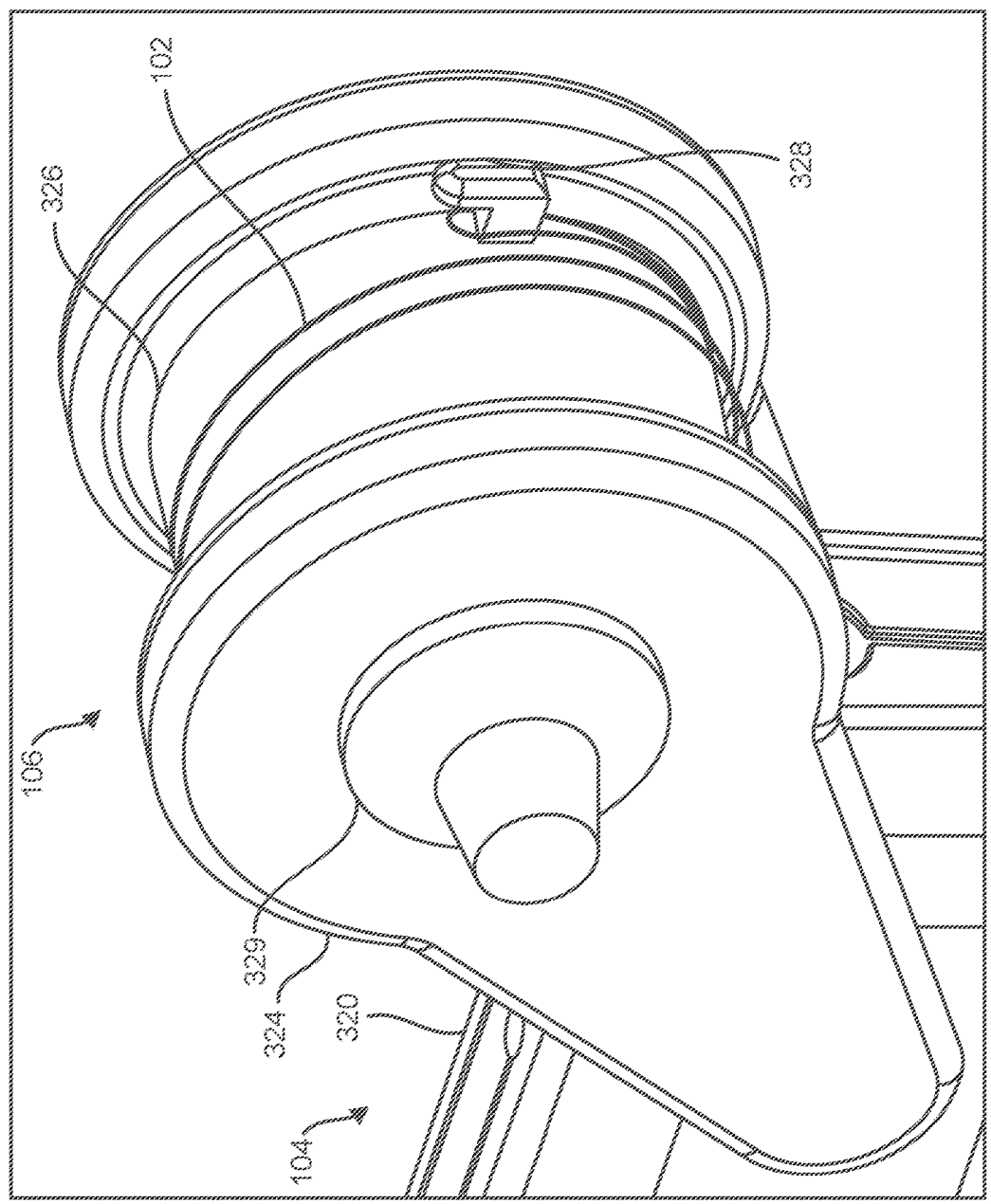
FIG. 4 illustrates a detail perspective view of the lead removal device and the traction applying device of the lead removal system of FIG. 1.

Referring now to FIGS. 3 and 4, the lead removal device 104 and the traction applying device 106 are illustrated. Generally, the lead removal device 104 includes a handle 320 coupled to the sheath 108. The handle 320 is configured to be grasped by a healthcare professional during a lead removal procedure. The handle 320 also includes a first user input 322 (for example, a trigger as illustrated; alternatively, a button, a switch, or the like) that is actuatable to actuate the distal separating member 112 and thereby separate a lead from adjacent tissue. As a specific example, the distal separating member 112 may be a mechanical cutting element, and actuation of the first user input 322 may actuate an internal drive mechanism (shown elsewhere) of the lead removal device 104, which in turn rotatably and/or translatably drives a mechanical cutting element and thereby separates a lead from adjacent tissue. As another specific example, the distal separating member 112 may be a laser-emitting element. Actuation of the first user input 322 may activate a laser generator (shown elsewhere) coupled to the lead removal device 104, which in turn delivers laser energy to the laser-emitting element, and the laser-emitting element emits laser energy and thereby ablates tissue adjacent to a lead. As another specific example, the distal separating member 112 may be a laser-emitting element, and the laser-emitting element emits laser energy upon actuation of a foot pedal (not shown) coupled to a laser generator. The above features of the lead removal device 104, and the lead removal device 104 more generally, may be similar to or the same as those described in U.S. Pat. Nos. 9,413,896; 9,603,618; 9,801,650; 9,918,737; 9,980,743; 10,136,913, or U.S. Patent Application Publication Nos. 2017/0172622; 2018/0221055, the disclosures of which are hereby incorporated by reference in their entireties.

With continued reference to FIGS. 3 and 4, the traction applying device 106 generally includes a frame 324 that is coupled to a proximal portion of the handle 320 of the lead removal device 104. The frame 324 may be fixed to or moveable relative to the handle 320. The traction applying device 106 may also include a mandrel 326 that is rotatably coupled to the frame 324. That is, the mandrel 326 rotates relative to the frame 324 and the handle 320.

Referring specifically to FIG. 4, the mandrel 326 includes a coupling feature 328 for coupling to the proximal coupling portion 218 of the lead engagement device 102. For example, and as illustrated in FIG. 4, the coupling feature 328 may be a hook that receives the loop of the lead engagement device 102. As the mandrel 326 rotates relative to the frame 324, the mandrel 326 winds the lead engagement device 102 therearound, thereby applying traction to the lead engagement device 102 and, in turn, to the lead.

In some embodiments and as illustrated, the traction applying device 106 includes an adjustment input 329 (for example, a dial or knob carried by the frame 324) for adjusting the amount of torque applied by the traction applying device 106 to the lead engagement device 102 and the lead. This may advantageously permit the traction applying device 106 to provide a first, relatively low torque (for example, 7 lb.-in.) in some situations (for example, when using the lead removal device 104 to separate tissue adjacent to a lead) and a second, intermediate torque (for example, 8.5 lb.-in.) and a third, relatively high torque (for example, 10 lb.-in.) in other situations (for example, after separating tissue adjacent to a lead and pulling an electrode coupled to the lead from the wall of a subject's heart). In other embodiments, the torque provided by the traction applying device 106 is non-adjustable. Although the adjustment input 329 is described as having three settings, the adjustment input may have additional settings or fewer settings (i.e., one or two settings). Also, although certain example torque values are identified as being associated with each of the three settings, other values may be associated with each setting. For example, each setting may be associated with a 1 lb.-in. such that if there are fifteen (15) settings, each setting corresponds to an equal amount of torque.

A second user input 330 coupled to the handle 320 (for example, a trigger as illustrated; alternatively, a button, a switch, or the like) is actuatable to rotate the mandrel 326 and thereby wind the lead engagement device 102 therearound. In some embodiments and as illustrated, the second user input 330 may be positioned relative to the first user input 322 such that both inputs may be actuated with the same hand. Further components and features of the traction applying device 106 are described below.

Figure 5:
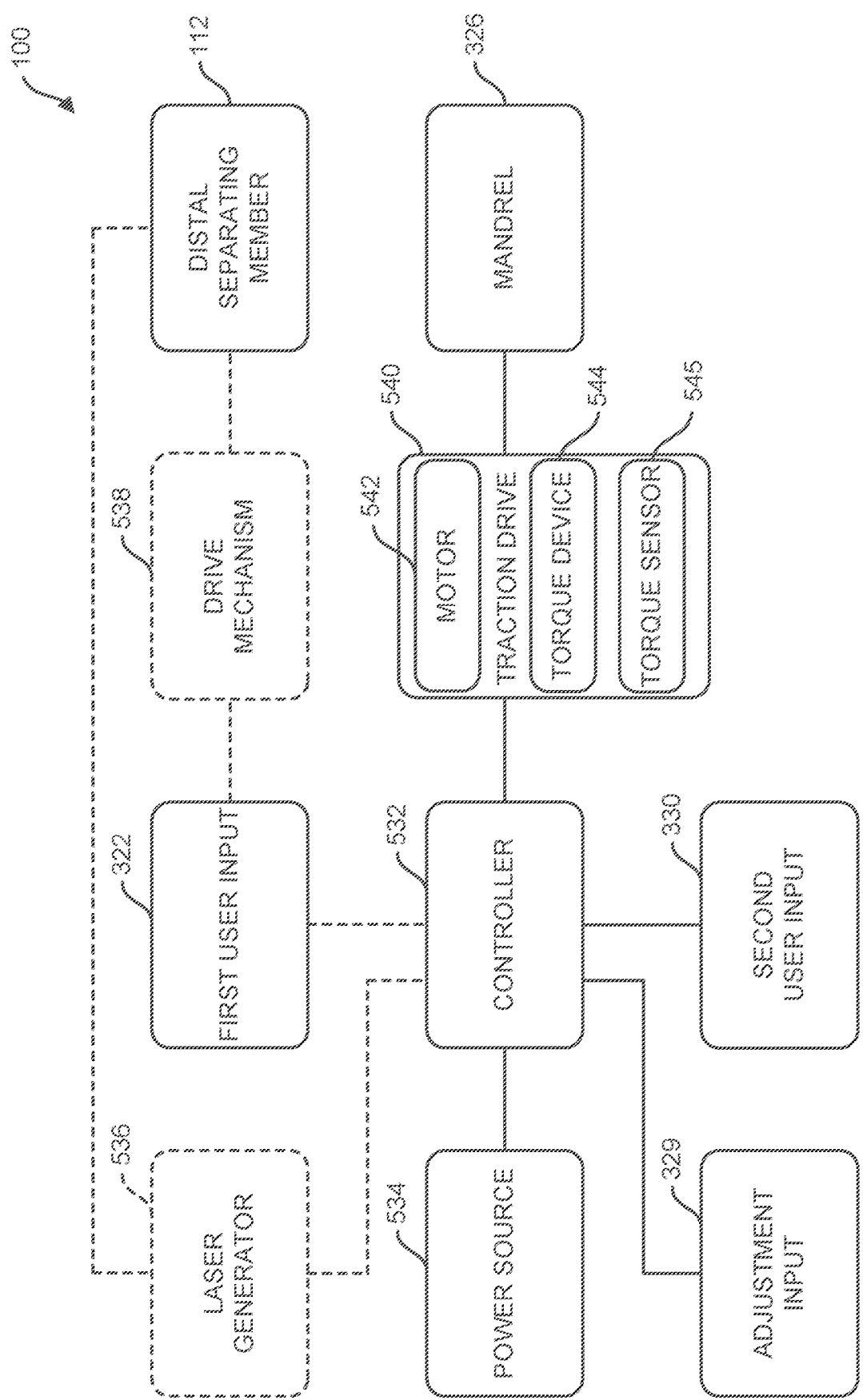
FIG. 5 illustrates a schematic of the lead removal system of FIG. 1.

FIG. 5 illustrates a schematic including operative connections between several components of the lead removal system 100. Such components include a microprocessor executable controller 532 (carried, for example, by the handle 320 of the lead removal device 104—see FIGS. 3 and 4). Generally, the controller 532 may include one or more processors, memory and one or more modules that contain logic or instructions stored in memory for controlling the operation of the lead engagement device 102, the lead removal device 104, and/or the traction applying device 106. For example, the controller 532 may include logic that coordinates the application of the amount of traction applied by traction applying device 106 to the lead extraction device 102. Accordingly, it is understood that any steps, data processing, instrument control, and/or other processing or control aspects of the present disclosure may be implemented by the computing systems using corresponding instructions stored on or in a non-transitory computer readable medium accessible by the controller 532 and/or another computing device.

The controller 532 receives power from a power source 534 (for example, a battery carried by the handle 320 of the lead removal, a plug configured to be coupled to a wall outlet, or the like). The controller 532 may also operatively couple to the first user input 322, for example, in embodiments in which the lead removal device 104 emits laser energy to ablate tissue adjacent to a lead. In such embodiments, actuation of the first user input 322 causes the controller 532 to energize a laser generator 536, which in turn delivers laser energy to the distal separating member 112 (more specifically, a laser-emitting element), and the distal separating member 112 emits laser energy and thereby ablates tissue adjacent to a lead. In other embodiments, for example, in which the lead removal device 104 mechanically cuts tissue adjacent to a lead, the controller 532 does not operatively couple to the first user input 322. Instead, actuation of the first user input 322 causes actuation of a drive mechanism 538 (carried, for example, by the handle 320 of the lead removal device 104—see FIGS. 3 and 4), which in turn drives the distal separating member 112 (more specifically, a mechanical cutting element) and thereby separates a lead from adjacent tissue.

The controller 532 operatively couples to the second user input 330. Actuation of the second user input 330 causes the controller 532 to energize a traction drive 540, which in turn rotates the mandrel 326 (to wind the lead engagement device 102 therearound and thereby apply traction to the lead engagement device 102 and the lead as described above—see FIGS. 3 and 4). The traction drive 540 may include, for example, a rotatable motor 542 that rotates the mandrel 326 (to wind the lead engagement device 102 therearound and thereby apply traction) and a torque sustaining device 544 (to sustain traction on the lead engagement device 102 and the lead), such as a disc brake, a drum brake, a variable pressure tensioner, a ratcheting device, or the like.

The traction drive system 540 may include a torque sustaining device 544 having a torque sensor 545 to monitor the amount of torque applied by the motor 542, which is coupled to the lead engagement device 102 and, in turn, to the lead. It may be desirable for the traction drive system 540 to apply a consistent and predetermined amount of torque (or a predetermined range of torque) to the lead engagement device 102 and the lead as the lead removal device 104 translates over the lead engagement device 102 and separates the lead from surrounding tissue. In some embodiments, the torque sensor 545 provides a torque signal to the controller 532, which monitors the amount of torque applied by the motor 542 and provides the corresponding amount of power to the rotatable motor 542 such that the motor 542 acts as the torque sustaining device 544 (and sustains a consistent amount of traction on the lead engagement device 102 and the lead).

With continued reference to FIG. 5, the lead removal system 100 may include an adjustment input 329 (for example, a dial or knob carried by the handle 320 of the lead removal device 104) for adjusting the torque provided by the traction drive 540 (and, accordingly, the traction applied to the lead engagement device 102 and the lead) as described above.

Figure 6:
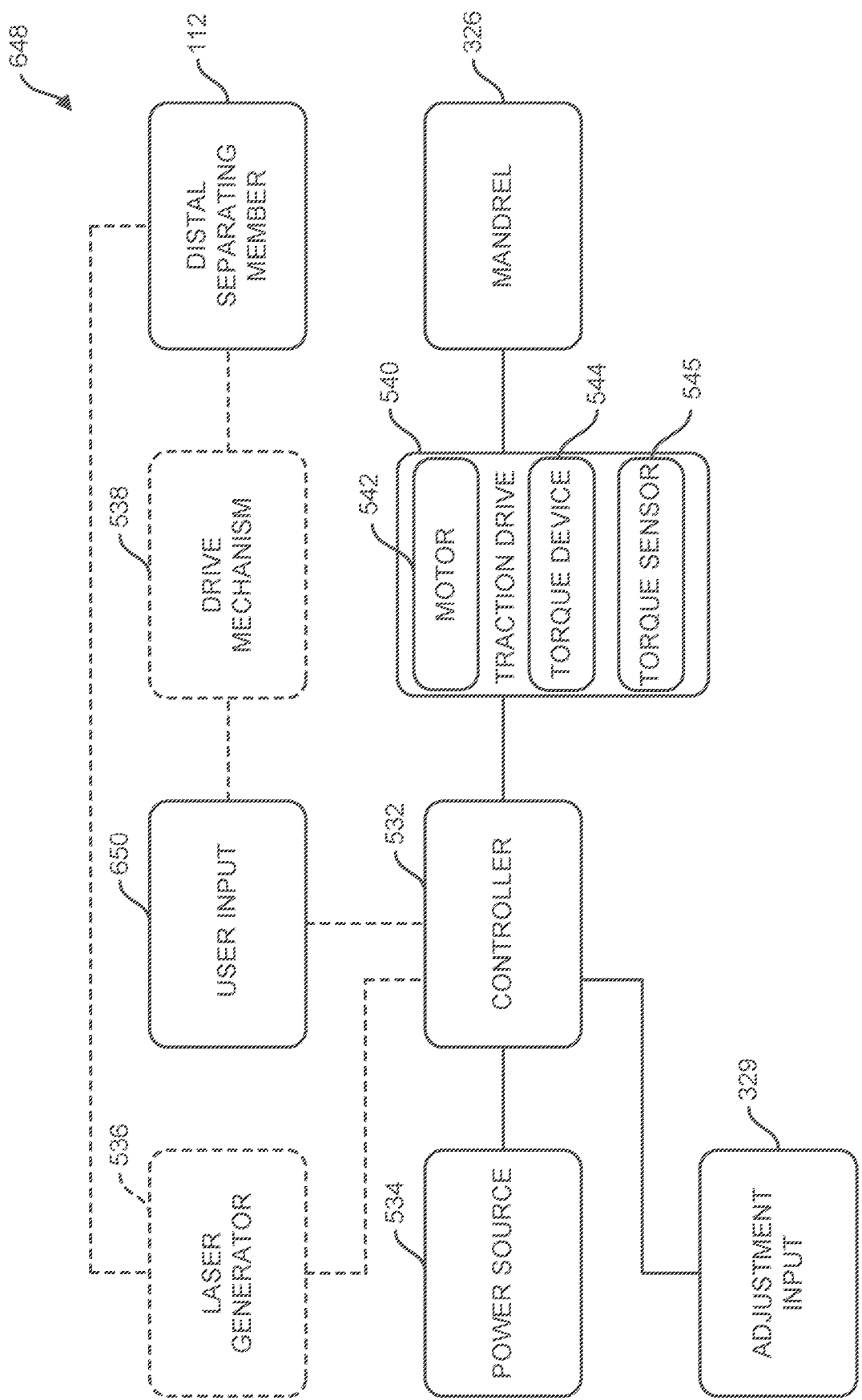
FIG. 6 illustrates a schematic of another embodiment of a lead removal system according to the present disclosure.

FIG. 6 illustrates a schematic including operative connections between several components of another embodiment of a lead removal system 648 according to the present disclosure. The lead removal system 648 includes many of the same components as the lead removal system 100 described above. As such, in FIG. 6 and in the following description, like components are identified with similar reference numbers. In contrast to the lead removal system 100, however, the lead removal system 648 only includes a single user input 650 for actuating both the distal separating member 112 and the traction applying device 106. That is, actuation of the user input 650 causes both the distal separating member 112 to separate tissue adjacent to a lead and the traction applying device 106 to apply traction to the lead engagement device 102 and the lead.

Embodiments of lead removal systems according to the present disclosure may take various other forms. For example, the traction drive may include a linear actuator for applying traction to the lead engagement device and a lead.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An apparatus for removing an implanted lead, the apparatus comprising:
a handle configured to be grasped by a user during a lead removal procedure to remove the implanted lead, wherein the implanted lead is coupled to a lead engagement device, wherein the lead engagement device comprises an elongated and flexible body configured to be inserted in a lead lumen of the implanted lead and secured to the implanted lead;
a frame coupled to the handle; and
a mandrel coupled to the frame, the mandrel configured to couple to the lead engagement device, wherein the mandrel is configured to rotate relative to the frame such that:
the lead engagement device is wound around the mandrel; and
the mandrel applies traction to the lead engagement device and the implanted lead,
wherein the handle comprises a controller configured to control the mandrel to rotate.

2. The apparatus of claim 1, wherein the frame is fixed to the handle.

3. The apparatus of claim 1, wherein the frame is movable relative to the handle.

4. The apparatus of claim 1, wherein the mandrel is configured to rotate relative to the handle.

5. The apparatus of claim 1, wherein the mandrel comprises a hook configured to receive a loop of the lead engagement device.

6. The apparatus of claim 1, wherein the frame comprises a dial or a knob configured to adjust a torque applied to the lead engagement device and the implanted lead.

7. The apparatus of claim 6, wherein the dial or the knob is configured to provide a plurality of pre-determined amounts of torque.

8. The apparatus of claim 1, wherein the handle comprises a trigger, a button, or a switch configured to cause the mandrel to rotate.

9. The apparatus of claim 1,
further comprising a sheath coupled to the handle,
wherein the sheath is configured to receive the lead engagement device and the implanted lead.

10. The apparatus of claim 9,
wherein the sheath is configured to separate the implanted lead from tissue,
wherein the handle comprises a trigger, a button, or a switch configured to cause the sheath to separate the implanted lead from the tissue.

11. The apparatus of claim 1,
wherein the handle comprises a motor coupled to the controller,
wherein the controller is configured to control the motor to cause the mandrel to rotate.

12. The apparatus of claim 11,
further comprising a torque sensor coupled to the controller,
wherein the controller is configured to control the motor based on a signal from the torque sensor.

* * * * *